United States Patent
Reid et al.

(10) Patent No.: US 7,626,092 B2
(45) Date of Patent: Dec. 1, 2009

(54) COTTON VARIETY FM 960B2R

(75) Inventors: Peter Reid, Narrabri (AU); Greg Constable, Narrabri (AU); Warwick Stiller, Narrabri (AU)

(73) Assignee: Commonwealth Scientific and Industrial Research Organization (CSIRO), Act Campbell (AU)

( * ) Notice: Subject to any disclaimer, the term of this patent is extended or adjusted under 35 U.S.C. 154(b) by 452 days.

(21) Appl. No.: 11/346,227

(22) Filed: Feb. 3, 2006

(65) Prior Publication Data

US 2006/0191046 A1    Aug. 24, 2006

Related U.S. Application Data

(60) Provisional application No. 60/649,739, filed on Feb. 3, 2005.

(51) Int. Cl.
*A01H 5/00* (2006.01)
*A01H 5/10* (2006.01)
*A01H 4/00* (2006.01)
*A01H 1/00* (2006.01)
*C12N 15/82* (2006.01)

(52) U.S. Cl. .................. 800/314; 800/260; 800/263; 800/264; 800/265; 800/269; 800/278; 800/279; 800/281; 800/284; 800/300; 800/301; 800/302; 435/410

(58) Field of Classification Search .......... 800/260, 800/263, 264, 265, 269, 278, 279, 281, 284, 800/300, 301, 302, 314; 435/410
See application file for complete search history.

(56) References Cited

U.S. PATENT DOCUMENTS 6,008,438 A * 12/1999 Keim .................... 800/314
6,740,488 B2   5/2004 Rangwala et al.
6,818,807 B2  11/2004 Trolinder et al.

2004/0148666 A1   7/2004 Rangwala et al.

FOREIGN PATENT DOCUMENTS

EP         0270355      6/1988
WO      WO 00/71733   11/2000

OTHER PUBLICATIONS

Dow AgroSciences, Risk assessment and risk management plan, DIR 040/2003, Nov. 2003, p. 25, paragraph 115.*
Plant Varieties Journal. Plant Varieties Journal, vol. 17, No. 3, Oct. 27, 2004.*
Plant Variety 'Sicala 60-BR'; *Plant Varieties Journal*, vol. 13, No. 3, pp. 168-170, (2004).
USDA APHIS Petition 94-308-01p (downloaded from USDA website on Jul. 7, 2006).
USDA APHIS Petition 00-342-01p (downloaded from USDA website on Jul. 7, 2006).
USDA APHIS Petition 95-045-01p (downloaded from USDA website on Jul. 7, 2006).
Plant Variety Protection No. 200100209 (FM 966) Date Issued: Aug. 27, 2004.
Plant Variety Protection No. 200500135 (FM 966LL) Date Filed: Feb. 14, 2005.
F.N. Briggs and P.F. Knowles, "Introduction to Plant Breeding," Chapters 11, 13 & 18, Reinhold Publishing Corporation, 1967.
H.F. Sakhanoko et al., "Induction of Somatic Embryogenesis and Plant Regeneration in Select Georgia and Pee Dee Cotton Lines." Crop Science 44: 2199-2205 (2004).
P. Stam, "Marker-assisted introgression: speed at any cost?" Proceedings of the Eucarpia Meeting on Leafy Vegetable Genetics and Breeding, Noordwijkerhout, The Netherlands, Mar. 19-21, 2003. Eds. Th.J. L. van Hintum, A. Lebeda, D. Pink, J.W. Schut. p. 117-124 (2003).

* cited by examiner

*Primary Examiner*—Anne Marie Grunberg
*Assistant Examiner*—Keith O. Robinson
(74) *Attorney, Agent, or Firm*—Hunton & Williams LLP

(57) ABSTRACT

A novel cotton variety, designated as FM 960B2R, is disclosed. The invention relates to seeds, plants, plant cells, plant tissue, harvested products and cotton lint as well as to hybrid cotton plants and seeds obtained by crossing plants of variety FM 960B2R with other plants. The invention also relates to plants and varieties produced by the method of essential derivation from plants of FM 960B2R and to plants of FM 960B2R reproduced by vegetative methods, including but not limited to tissue culture of regenerable cells or tissue from FM 960B2R.

17 Claims, No Drawings

COTTON VARIETY FM 960B2R

CROSS-REFERENCE TO RELATED APPLICATIONS

This application claims the benefit of U.S. Provisional Application No. 06/649,739, filed Feb. 3, 2005, the disclosure of which is herein incorporated by reference in its entirety.

BACKGROUND OF THE INVENTION (i) Field of the Invention

This invention relates to the field of plant breeding. More particularly, the invention encompasses a variety of cotton designated as FM 960B2R, its essentially derived varieties and the hybrid varieties obtained by crossing FM 960B2R as a parent line with plants of other varieties or parent lines.

(ii) Description of the Related Art

Cotton is an important, fiber producing crop. In particular, due to the importance of cotton to the textile industry, cotton breeders are increasingly seeking to obtain healthy, good yielding crops of an excellent quality. Cotton is commonly reproduced by self-pollination and fertilization. This type of sexual reproduction facilitates the preservation of plant and variety characteristics during breeding and seed production. The preservation of these characteristics are often important to plant breeders for producing cotton plants having desired traits. Other methods of producing cotton plants having desired traits are also used and include methods such as genetic transformation via *Agrobacterium* infection or direct transfer by microparticle bombardment.

Due to the environment, the complexity of the structure of genes and location of a gene in the genome, among other factors, it is difficult to predict the phenotypic expression of a particular genotype. In addition, a plant breeder may only apply his skills on the phenotype and not, or in a very limited way, on the level of the genotype. Because of this phenomenon, a plant breeder cannot breed the same variety twice using the same parents and the same methodology, thus a newly bred variety is considered to be an unexpected result of the breeding process. In particular, each variety will typically contain a unique combination of known or novel characteristics.

However, by carefully choosing the breeding parents, the breeding and selection methods, the testing layout and testing locations, the breeder may breed a particular variety type. In addition, the new variety may be tested in special comparative trials with other existing varieties in order to determine whether the new variety meets the required expectations.

SUMMARY OF THE INVENTION

The present invention relates to seeds, plants, plant cells, parts of plants, cotton lint or fiber, and cotton textiles of the cotton variety designated as FM 960B2R, as well as to hybrid cotton plants and seeds obtained by (repeatedly) crossing plants of FM 960B2R with other cotton plants. The invention encompasses plants and plant varieties produced by the method of essential derivation from plants of FM 960B2R and to plants of FM 960B2R reproduced by vegetative methods, including but not limited to, regeneration of embryogenic cells or tissue of FM 960B2R.

DETAILED DESCRIPTION OF PREFERRED EMBODIMENTS

As used herein, "cotton" refers to plants, seeds or plant cells of the genus *Gossypium*, preferably the species *Gossypium hirsutum*.

As used herein, "lint" refers to the mass of soft fibers surrounding the seeds of unginned cotton.

As used herein, "phenotypic characteristics" refers to the observable, measurable or otherwise determinable physical or biochemical characteristics of an organism, as determined by both genetic makeup and environmental influences (e.g., length, color, size, weight, biochemical composition, protein concentration, etc.).

As used herein, "fiber" refers to the natural filament of cotton, capable of being spun into yarn, as is typically separated from unginned cotton seed.

The invention has been obtained by a general breeding process comprising the steps outlined below. (For reference, see Chapter 11, "Breeding Self-Pollinated Crops by Hybridization and Pedigree Selection," in F. N. Briggs and P. F Knowles (1967)).

Parent plants, which have been selected for good agronomic and fiber quality traits are manually crossed in different combinations. The resulting F1 (Filial generation 1) plants are self fertilized and the resulting F2 generation plants, which show a large variability on account of optimal gene segregation, are planted in a selection field.

These F2 plants are observed during the growing season for health, growth vigor, plant type, plant structure, leaf type, stand ability, flowering, maturity, seed yield, boll type, boll distribution, boll size, fiber yield and fiber quality. Plants are then selected. The selected plants are harvested, the bolls are analyzed for fiber characteristics and the seeds are cleaned and stored. This procedure is repeated in the following growing seasons, whereby the selection and testing units increase from individual plants in the F2, to multiple plants containing 'lines' (descending from one mother plant) in the F5 and the number of units decrease from approximately 2500 plants in the F2 to 20 lines in the F5 by selecting about 10-20% of the units in each selection cycle.

The increased size of the units, whereby more seed per unit is available, allows the selection and testing in replicated trials on more than one location with a different environment and a more extensive and accurate analyzing of the fiber quality.

The lines or candidate varieties become genotypically more homozygous and phenotypically more homogeneous by selecting similar plant types within a line and by discarding the so called off-types from the very variable F2 generation on to the final F7 or F8 generation.

Depending on the intermediate results the plant breeder may decide to vary the procedure as described above such as by accelerating the process by testing a particular line earlier or retesting a line another year. He may also select plants for further crossing with existing parent plants or with other plants resulting from the current selection procedure.

By the method of recurrent backcrossing, as described by Briggs and Knowles, supra, in Chapter 13, "The Backcross Method of Breeding," the breeder may introduce a specific trait or traits into an existing, valuable line or variety, while otherwise preserving the unique combination of characteristics of this line or variety. In this crossing method, the valuable parent is recurrently used to cross it at least for three times with each resulting backcross F1, followed by selection of the recurrent parent plant type, until the phenotype of the resulting F1 is similar or almost identical to the phenotype of the recurrent parent with the addition of the expression of the desired trait or traits.

This method of recurrent backcrossing eventually results in an essentially derived variety, which is predominantly derived from the recurrent parent or initial variety. This method can therefore also be used to get as close as possible to the genetic composition of an existing successful variety. Thus, compared to the recurrent parent the essentially derived variety retains a distinctive trait, which can be any phenotypic trait, with the intention to profit from the qualities of that successful initial variety.

Depending on the number of backcrosses and the efficacy of the selection of the recurrent parent plant type and genotype, which can be supported by the use of molecular markers as described by P. Stam (2003), the genetic conformity with the initial variety of the resulting essentially derived variety may vary between 90% and 100%.

Except via recurrent backcrossing, as described above, such essentially derived variety may also be obtained by the selection from an initial variety of an induced or natural occurring mutant plant, an occurring variant (off-type) plant, a somaclonal variant plant or by genetic transformation of regenerable plant tissue or embryogenic cell cultures of the said initial variety by methods well known to those skilled in the art, such as, for example, by *Agrobacterium*-mediated transformation as described by Sakhanokho et al. (2004), Reynaerts et al. (2000), Umbeck et al. (1988) and others. Examples of transgenic Events transformed in this way are "LLCotton25," USDA-APHIS petition 02-042-01p, "Cot 102," USDA-APHIS petition 03-155-01p and "281-24-236," USDA-APHIS petition 03-036-01p, combined with "3006-210-23," USDA-APHIS petition 03-036-02p. Information regarding these and other transgenic events referred to herein may be found at the U.S. Department of Agriculture's (USDA) Animal and Plant Health Inspection Service (APHIS) website. An "Event" is defined as a (artificial) genetic locus that, as a result of genetic engineering, carries a foreign DNA comprising at least one copy of the gene(s) of interest.

The plants selected or transformed retain the unique combination of characteristics of 960B2R, except for the different expression of one, two, three, four or five characteristics changed by the selection of the mutant or variant plant or the one, two, three, four or five different characteristics added, e.g., by genetic transformation.

The product of essential derivation is an essentially derived variety, which is, except for the one, two, three, four or five distinctive characteristics, which characteristics are different as the result of the act of derivation, characterized by the same combination of expression of the characteristics in its phenotype as in the phenotype of the initial variety, which same combination of expression results from the genotype that is nearly identical or almost identical or similar to the genotype of the initial variety. Plants of the essentially derived variety can be used to repeat the process of essential derivation. The result of this process is also a variety essentially derived from said initial variety.

FM 960B2R has been obtained by introducing the Events "MON531" (USDA-APHIS petition 94-308-01p, the disclosure of which is herein incorporated by reference in its entirety) in combination with "MON15985" (USDA-APHIS petition 00-342-01p, the disclosure of which is herein incorporated by reference in its entirety) and "MON1445" (USDA-APHIS petition 95-045-01p, see also Publication No. US 2004/0148666 and U.S. Pat. No. 6,740,488, the disclosure of each of which is herein incorporated by reference in their entireties), via a cross between a donor plant containing these Events and the cotton variety "FM 966" (USA Plant Variety Protection Number 200100209, filed May 29, 2001, issued: Aug. 27, 2004), followed by three backcrosses of the F1 plants resulting from these crosses, that express the characteristics of FM 966 combined with the Events as described above, with plants of FM 966. The resulting variety FM 960B2R is similar to the existing variety FM 966, but differs by its resistance to the insect pests Cotton Bollworm, Cotton Leafworm, Fall Armyworm, Pink Bollworm and Tobacco Budworm, as a result of the surprising expression of the Events MON531 and MON15985 in combination with the remainder of the characteristics of FM 966 and the resistance to the herbicide glyfosate as a result of the surprising expression of the Event MON 1445 in combination with the remainder of the characteristics of FM 966.

Provided herein as embodiments of the invention are seeds, plants, plant cells and parts of plants of the cotton variety FM 960B2R. Representative seeds of this variety have been deposited with the NCIMB Ltd. (Ferguson Building, Craibstone Estate, Bucksburn, Aberdeen, AB21 9YA, Scotland, UK), under the Budapest Treaty, on Jan. 3, 2007, under NCIMB Accession No. 41457. Plants produced by growing such seeds are provided herein as embodiments of the invention. Also provided herein are pollen or ovules of these plants, as well as a cell or tissue culture of regenerable cells from such plants. In another embodiment, the invention provides for a cotton plant regenerated from such cell or tissue culture, wherein the regenerated plant has the morphological and physiological characteristics of cotton cultivar FM960B2R, as described in the FM960B2R variety characteristics in Table 1, when grown in the same environmental conditions. In yet another embodiment, the invention provides methods of testing for a plant having the morphological and physiological characteristics of cotton cultivar FM960B2R. In one embodiment, the testing for a plant having the morphological and physiological characteristics of cotton cultivar FM960B2R is carried out in the same field, under the same conditions and in the presence of plants of FM960B2R, e.g., plants grown from the seed deposited under NCIMB Accession number 41457. In another embodiment, the characteristics to be tested for are those listed in Table 1.

Another embodiment of the invention provides for a method of introducing a desired trait into cotton cultivar FM960B2R comprising: (a) crossing the FM960B2R plants, grown from seed deposited under NCIMB Accession No. 41427, with plants of another cotton line that comprise a desired trait to produce F1 progeny plants, wherein the desired trait is selected from the group consisting of male sterility, herbicide resistance, insect resistance and resistance to bacterial, fungal or viral disease; (b) selecting F1 progeny plants that have the desired trait to produce selected F1 progeny plants; (c) crossing the selected F1 progeny plants with the FM960B2R plants to produce first backcross progeny plants; (d) selecting for first backcross progeny plants that have the desired trait and the physiological and morphological characteristics of cotton cultivar FM960B2R as described in the FM960B2R variety characteristics in Table 1, when grown in the same environmental conditions, to produce selected first backcross progeny plants; and (e) repeating steps (c) and (d) two or more times in succession to produce selected third or higher backcross progeny plants that comprise the desired trait and all of the physiological and morphological characteristics of cotton cultivar FM960B2R as described in the FM960B2R variety characteristics in Table 1, when grown in the same environmental conditions. Also included herein is a plant produced by this method, wherein such plant has the desired trait and all of the physiological and morphological characteristics, when grown in the same environmental conditions, of cotton cultivar FM960B2R, representative seed of which having been deposited under NCIMB Accession No. 41457.

Also included herein is a method of producing cotton seed, comprising the steps of using the plant grown from seed of cotton variety FM 960B2R, of which a representative seed sample has been deposited under NCIMB Accession No. 41457, as recurrent parent in crosses with other cotton plants different from FM 960B2R, and harvesting the resultant cotton seed.

Another embodiment of this invention relates to seeds, plants, plant cells and parts of plants of cotton varieties that are essentially derived from FM 960B2R, being essentially the same as this invention by expressing the unique combination of characteristics of FM 960B2R, including the insect resistance and herbicide resistance of FM 960B2R, except for one, two, three, four or five characteristics being different from the characteristics of FM 960B2R as a result of the act of derivation.

Another embodiment of this invention is the reproduction of plants of FM 960B2R by the method of tissue culture from any regenerable plant tissue obtained from plants of this invention. Plants reproduced by this method express the specific combination of characteristics of this invention and fall within its scope. During one of the steps of the reproduction process via tissue culture somaclonal, variant plants may occur, which plants can be selected as being distinct from this invention, but still fall within the scope of this invention as being essentially derived from this invention.

Another embodiment of this invention is the production of a hybrid variety comprising (repeatedly) crossing plants of FM 960B2R with plants of a different variety or varieties or with plants of a non-released line or lines. In practice, three different types of hybrid varieties may be produced (see e.g., Chapter 18, "Hybrid Varieties" in Briggs and Knowles, supra):

The "single cross hybrid" produced by two different lines, the "three way hybrid," produced by three different lines such that first the single hybrid is produced by using two out of the three lines followed by crossing this single hybrid with the third line and the "four way hybrid" produced by four different lines such that first two single hybrids are produced using the lines two by two, followed by crossing the two single hybrids so produced.

Each single, three way or four way hybrid variety so produced and using FM 960B2R as one of the parent lines contains an essential contribution of FM 960B2R to the resulting hybrid variety and falls within the scope of this invention.

Cotton lint or fiber produced by the plants of this invention and by plants reproduced from this invention and by plants essentially derived from this invention have the unique combination of the quality characteristics of FM 960B2R and fall within the scope of this invention. The final textile produced form the unique fiber of FM 960B2R also falls within the scope of this invention.

It will be clear that the invention may be practiced otherwise than as particularly described in the foregoing description and examples. Numerous modifications and variations of the present invention are possible in light of the above teachings and, therefore, are within the scope of the appended claims.

The entire disclosure of each document cited (including patents, patent applications, journal articles, abstracts, laboratory manuals, books or other disclosures) in the Background of the Invention, Detailed Description and Examples is hereby incorporated herein by reference.

EXAMPLE 1

Seeds of the variety FM 960B2R (a representative sample of such seeds deposited under NCIMB Accession No. 41457) were planted, together with seeds of cotton variety DP555BGR as a reference variety, in field trials at two locations, as mentioned hereunder.

The results as shown in Table 1 and 2 were obtained from a pooled analysis of the data from these two trials:

1. BCSI Research Station, Leland MS, 2004. Conditions: field grown irrigated trial with conventional management. Trial design: 5 entry trial in a row and column design with six replicates and 14 m plots. Measurements on 10 plants from each plot.

2. Australian Cotton Research Institute, Narrabri, NSW, 2003/04 summer. Conditions: field grown irrigated trial with conventional management. Trial design: 24 entry trial in a row and column design with six replicates and two rows×14 m plots. Measurements on 10 plants from each plot.

Analysis of variance procedures were used to obtain least significant difference statistics at the 1% level.

The description as mentioned in Table 1 and 2 reflect the average expression of the characteristics of FM 960B2R on these locations in 2003/2004. This expression can be different on other locations and/or in other years. The sample that will be deposited represents the variety and this sample can be analyzed for the expression of its phenotypic characteristics at any time and at any location.

TABLE 1

Descriptive Characteristics of FM 960B2R

| | | Variety | |
| --- | --- | --- | --- |
| Description of Characteristic | possible expression/note | FM 960B2R | DP555BG/RR |
| General Plant Type | | | |
| Plant Habit | spreading, intermediate, compact | intermediate | intermediate |
| Foliage | sparse, intermediate, dense | intermediate | intermediate |
| Stem Lodging | lodging, intermediate, erect | intermediate | erect |
| Fruiting Branch | clustered, short, normal | normal | normal |
| Growth | determinate, intermediate, inderminate | intermediate | indeterminate |
| Leaf color | greenish yellow, light green, medium green, dark green | medium green | medium green |

TABLE 1-continued

Descriptive Characteristics of FM 960B2R

| Description of Characteristic | possible expression/note | Variety | |
|---|---|---|---|
| | | FM 960B2R | DP555BG/RR |
| Boll Shape | Length < Width, L = W, L > W | L > W | L > W |
| Boll Breadth | broadest at base, broadest at middle | broadest middle | broadest middle |
| Maturity | date of 50% open bolls | September 27 | October 4 |
| Plant | | | |
| cm. to first Fruiting Branch | from cotyledonary node | 19.8 | 23.3 |
| No. of nodes to 1st Fruiting Branch | excluding cotyledonary node | 7.0 | 7.3 |
| Mature Plant Height in cm. | cotyledonary node to terminal | 108.2 | 132.8 |
| Leaf: upper most, fully expanded | | | |
| Type | normal, sub-okra, okra, super-okra | normal | normal |
| Pubescense | absent, sparse, medium, dense | sparse | sparse |
| Nectaries | present, absent | present | present |
| Stem Pubescense | glabrous, intermediate, hairy | intermediate | intermediate |
| Glands (Gossypol) | absent, sparse, normal, more than normal | | |
| Leaf | | normal | normal |
| Stem | | normal | normal |
| Calyx lobe | (normal is absent) | normal | normal |
| Flower | | | |
| Petals | cream, yellow | cream | cream |
| Pollen | cream, yellow | cream | cream |
| Petal Spot | present, absent | absent | absent |
| Peduncle Length (mm) | | 23.7 | 20.2 |
| Stigma Distance above Stamens (mm) | | 5.7 | 3.4 |
| Seed | | | |
| Seed Index | g/100 seed fuzzy basis | 12.3 | 8.9 |
| Lint Index | g lint/100 seeds | 8.6 | 6.9 |
| Boll | | | |
| Gin | picked, stripped | picked | |
| Gin Turnout (%) | | 36.7 | 43.1 |
| Number of Seeds per Boll | | 25.8 | 28.1 |
| Grams Seed Cotton per Boll | | 5.4 | 4.6 |
| Number of Locules per Boll | | 4.1 | 4.2 |
| Boll Type | storm proof, storm resistant, open | storm resistant | open |
| Fiber Properties | | | |
| Method | HVI or Other | HVI | |
| Length | inches, 2.5% SL | 1.18 | 1.15 |
| Uniformity | % | 85.3 | 83.0 |
| Strength, T1 | g/tex | 30.3 | 26.5 |
| Elongation, E1 | % | 5.9 | 7.0 |
| Micronaire | | 4.2 | 4.4 |
| Diseases, Insects and Pests | susceptible = S, moderately susceptible = MS moderately resistant = MR, resistant = R | | |
| Bacterial Blight race 1 | | R | |
| Bacterial Blight race 2 | | R | |
| Bacterial Blight Race 18 | | R | |
| Verticillium Wilt | | MR | |
| Bollworm | | R | |
| Cotton Leafworm | | R | |
| Fall Armyworm | | R | |
| Pink Bollworm | | R | |
| Tobacco Budworm | | R | |

TABLE 2

Distinguishing Characteristics of FM 960B2R

| Characteristic | Variety | |
| --- | --- | --- |
| | FM 960B2R | DP 555BG/RR |
| Bollgard II gene (Cry2Ab) | Present | Absent |
| Height to first Fruiting Branch (cm) | | |
| Mean | 19.8 | 23.3 |
| Range | 17.4-22.7 | 20.6-26.0 |
| LSD (1%) | 2.47 | |
| Significance | | $P < 0.01$ |
| Plant Height (cm) | | |
| Mean | 108.2 | 132.8 |
| Range | 102.7-112.4 | 119-141 |
| LSD (1%) | 7.62 | |
| Significance | | $P < 0.01$ |
| Stigma Distance above Stamens (mm) | | |
| Mean | 4.8 | 3.4 |
| Range | 4.0-5.1 | 2.0-4.8 |
| LSD (1%) | 0.82 | |
| Significance | | $P < 0.01$ |
| Lint Percentage | | |
| Mean | 36.7 | 43.1 |
| Range | 35.5-37.3 | 41.7-44.7 |
| LSD (1%) | 1.34 | |
| Significance | | $P < 0.01$ |

EXAMPLE 2

A variety essentially derived from FM 960B2R is obtained by the process of the transgression of the Event LLCotton 25 (USDA-APHIS petition 02-042-01p, see also U.S. Pat. No. 6,818,807, the disclosure of each of which is herein incorporated by reference in their entireties), into plants of the variety FM 960B2R via the method of recurrent backcrossing and selecting the plants which express the characteristics of FM 960B2R combined with the resistance to the herbicide glufosinate.

EXAMPLE 3

A variety essentially derived from FM 960B2R is obtained by the process of the transgression of the Event LLCotton 25 via genetic engineering in regenerable cells or tissue of FM 960B2R and the subsequent selection of regenerated plants, which express the characteristics of FM 960B2R combined with the resistance to the herbicide glufosinate.

EXAMPLE 4

A variety essentially derived from FM 960B2R is obtained by the selection of an induced or natural occurring mutant plant or off-type plant from plants of FM 960B2R, which plant retains the expression of the phenotypic characteristics of FM 960B2R and differs only from FM 960B2R in the expression of one, two, three, four or five of the characteristics as listed in table 1, and when grown side by side with FM 960B2R on one or two locations in one or two growing seasons.

CITED REFERENCES

F. N. Briggs and P. F. Knowles, "Introduction to Plant Breeding." Rheinhold Publishing Corporation, 1967.

H. F. Sakhanoko et al., "Induction of Somatic Embryogenesis and Plant Regeneration in Select Georgia and Pee Dee Cotton Lines." Crop Science 44: 2199-2205 (2004).

Umbeck et al., "Genetic Engineering of Cotton Plants and Lines." Published patent Application Number EP0290355 (1988).

Reynaerts et al., "Improved Method for *Agrobacterium* Mediated Transformation of Cotton." International Publication Number WO 00/71733 (2000).

P. Stam, "Marker-assisted introgression: speed at any cost?" Proceedings of the Eucarpia Meeting on Leafy Vegetable Genetics and Breeding, Noordwijkerhout, The Netherlands, 19-21 Mar. 2003. Eds. Th. J. L. van Hintum, A. Lebeda, D. Pink, J. W. Schut. P117-124 (2003).

Trolinder et al. "Herbicide tolerant cotton plants having event EE-GH 1." U.S. Pat. No. 6,818,807 (2004).

Rangwala et al. "Cotton Event PV-GHGT07(1445) Compositions and Methods for Detection thereof." U.S. Pat. No. 6,740,488 (2004).

Rangwala et al. "Cotton Event PV-GHGT07(1445) Compositions and Methods for Detection thereof." Publication No. US 2004/0148666.

What is claimed is:

1. A seed of cotton variety FM 960B2R wherein a representative seed of said variety was deposited under NCIMB Accession No. 41457.

2. A plant, or a part thereof, produced by growing the seed of claim 1.

3. A plant, or a part thereof, obtained by vegetative reproduction from the plant, or a part thereof, of claim 2, said plant, or a part thereof, expressing all the phenotypic characteristics of cotton variety FM 960B2R, a sample of seed having been deposited under NCIMB Accession No. 41457.

4. A process of vegetative reproduction of cotton variety FM 960B2R comprising, culturing regenerable cells or tissue from FM 960B2R, a sample of seed having been deposited under NCIMB Accession No. 41457.

5. A cell or tissue culture produced from the plant, or a part thereof, of claim 2.

6. A cotton plant regenerated from the cell or tissue culture of claim 5, said plant expressing all the phenotypic characteristics of FM 960B2R, a sample of seed having been deposited under NCIMB Accession No. 41457.

7. A method of producing a F1 hybrid cotton seed, comprising the steps of crossing the plant of claim 2 with a different cotton plant and harvesting the resultant F1 hybrid cotton seed.

8. A F1 hybrid cotton seed produced by the method of claim 7.

9. A F1 hybrid cotton plant, or a part thereof, produced by growing the hybrid seed of claim 8.

10. A plant obtained by the vegetative reproduction of the cotton plant of claim 9.

11. A method of producing a cotton seed comprising the steps of crossing the plant of claim 9 with a different cotton plant and harvesting the resultant cotton seed.

12. A method of introducing a desired trait into a cotton plant, the method comprising transforming the plant of claim 2 with a transgene that confers the desired trait, wherein the transformed plant retains all the phenotypic characteristics of cotton variety FM 960B2R and contains the desired trait.

13. The method of claim 12, wherein said desired trait is herbicide resistance, insect resistance, bacterial disease resistance or fungal disease resistance.

14. The method of claim 12, wherein the desired herbicide resistance is an expression of the Event "LLCotton25" or the Event "MON88913" and the desired insect resistance is an expression of the Event "281-24-236", Event "3006-210-23" or a combination thereof or of the Event "Cot 102".

15. A method of introducing a desired trait into a cotton plant, the method comprising
transforming the plant of claim 6 with a transgene that confers the desired trait, wherein the transformed plant retains all the phenotypic characteristics of cotton variety FM 960B2R and contains the desired trait, seed of said variety having been deposited as NCIMB Accession No. 41457.

16. A cotton plant produced by the method of claim 12.

17. A plant produced by the method of claim 15.

* * * * *

UNITED STATES PATENT AND TRADEMARK OFFICE
CERTIFICATE OF CORRECTION

PATENT NO. : 7,626,092 B2  Page 1 of 1
APPLICATION NO. : 11/346227
DATED : December 1, 2009
INVENTOR(S) : Reid et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 753 days.

Signed and Sealed this

Second Day of November, 2010

David J. Kappos
*Director of the United States Patent and Trademark Office*